United States Patent
Shimoji

[11] Patent Number: 6,099,520
[45] Date of Patent: Aug. 8, 2000

[54] METHOD OF USING A CORDLESS MEDICAL LASER TO CURE COMPOSITES AND STERILIZE LIVING TISSUE

[76] Inventor: Yutaka Shimoji, 2125 University Ct., Clearwater, Fla. 33764

[21] Appl. No.: 09/107,623

[22] Filed: Jun. 30, 1998

Related U.S. Application Data

[63] Continuation-in-part of application No. 08/872,085, Jun. 10, 1997, Pat. No. 5,928,220.

[51] Int. Cl.$^7$ .................................................. A61B 18/18
[52] U.S. Cl. .................................. 606/2; 606/13; 606/17; 433/29; 433/215; 433/216
[58] Field of Search .................................. 606/2, 3, 8–10, 606/13–18; 607/89, 90, 93, 94; 433/29–31, 215, 221, 226, 228.1; 250/455.11

[56] References Cited

U.S. PATENT DOCUMENTS

| | | |
|---|---|---|
| 4,808,789 | 2/1989 | Muncheryan . |
| 4,940,411 | 7/1990 | Vassiliadis et al. ..................... 433/215 |
| 5,292,346 | 3/1994 | Ceravolo ..................... 606/2 |
| 5,401,171 | 3/1995 | Paghdiwala ..................... 433/215 |
| 5,456,603 | 10/1995 | Kowalyk ..................... 433/215 |
| 5,464,436 | 11/1995 | Smith ..................... 607/89 |
| 5,507,739 | 4/1996 | Vassiliadis et al. ..................... 606/3 |
| 5,616,141 | 4/1997 | Cipolla ..................... 606/15 |
| 5,803,729 | 9/1998 | Tsimerman ..................... 606/2 |
| 5,928,220 | 7/1999 | Shimoji ..................... 606/2 |

*Primary Examiner*—Linda C. M. Dvorak
*Assistant Examiner*—Bryan K. Yarnell

[57] ABSTRACT

A controlled process for thoroughly curing light-activated surgical and dental composites and a process for tissue sterilization is presented using a hand-held, self-contained, cordless, rechargeable laser instrument. At least one solid state microchip laser is pumped by at least one diode laser to generate blue laser light of at most 480 nm. Q-switched, pulsed laser light output enhances efficiency and control of the curing. Another microchip laser within the instrument generates 210–360 nm wavelength of UV laser light for the sterilization process which differentially kills microbiological life forms contaminating a repair site without killing healthy tissue. The process of use includes switching from sterilization mode to curing mode of operation of the instrument to save time during surgical and dental procedures.

4 Claims, 1 Drawing Sheet

6,099,520

METHOD OF USING A CORDLESS MEDICAL LASER TO CURE COMPOSITES AND STERILIZE LIVING TISSUE

RELATED PATENT CROSS REFERENCE

This application is a continuation-in-part of U.S. patent application Ser. No. 08/872,085, now U.S. Pat. No. 5,928,220 entitled "Cordless Dental and Surgical Laser", filed on Jun. 10, 1997.

BACKGROUND

The present invention relates to a method of using a medical laser instrument for curing dental and surgical composite materials and for sterilizing living tissue, which provides single line laser light generation from diode pumped solid state microchips.

Cipolla discloses in U.S. Pat. No. 5,616,141 an argon laser dental instrument and method for curing dental composites. However, the laser light consists of multi-line bands of wavelength, of which some wavelength lines must be filtered, since they are not useful for the purpose of curing. Therefore, the system displays an inefficient way of producing the laser line necessary for the curing. In addition, the laser system is an argon gas laser for which a high power cooling system must be supplied in order to operate it. Furthermore, the argon gas laser requires high voltage and a high current power source. Therefore, the instrument can not be made into a compact, hand-held, self-contained unit. A large stationary unit is required to be connected to a separate hand-held portion by optic fibers and cables. Furthermore, the output of the argon laser consists of many lines of wavelength from blue to green of which only the blue line of 488 nm is useful for curing. The beam is collimated and, therefore, has constant power along the propagation length of the beam. This results in uncontrolled curing and air bubble entrapment due to the fact that the surface layers begin to cure prior to the deeper layers.

Vassiliadis et al. in U.S. Pat. No. 4,940,411 discloses a method of eradicating and sterilizing pulp tissue using a pulsed Nd:YAG laser at 1.06$\mu$. The unit is not self-contained and cordless, and the wavelength generated can not be used to cure composites. Also, the sterilization is done by obliteration and cauterization and can not be done without killing living tissue. Also disclosed is a dual wavelength laser in U.S. Pat. No. 5,507,739 for dental therapy, but these are 1.06$\mu$ and 1.32$\mu$ infrared wavelengths which are not useful for curing composites nor for sterilization of tissue.

Paghdiwala discloses a focused pulsed Er:YAG laser for cutting in dental applications in U.S. Pat. No. 5,401,171. The laser light is generated within a hand-held tool, but the power supply and water cooling pump are external and not self-contained in a hand-held instrument and there is no method disclosed for curing composites nor for tissue sterilization.

Kowalyk et al. discloses a method for removing tooth decay in U.S. Pat. No. 5,456,603 using pulsed, frequency doubled lasers emitting red, green, deep blue, and UV light attenuated by some dye material. Consequently, none of wavelengths described in the patent match the maximum absorption wavelength of medical composites for curing. The device is not a compact, hand-held, self-contained instrument.

Therefore, there remains a need to provide an efficient method for laser curing of dental and surgical composite materials and for laser sterilization of tissue in a cordless, portable, selfcontained, hand-held instrument which generates a single, optimum wavelength for each use.

SUMMARY

An object of the present invention is to provide a practical and efficient method for curing medical composites with laser light.

Another object of the invention is to provide a method for sterilizing living biological tissue quickly and effectively with laser light without killing living tissue.

Another object of the invention is to provide a method of curing medical composite materials that overcomes the problems of incomplete curing, etc. of the prior art.

Another object of the invention is to provide a method of sterilizing tissue and curing medical composites in a single instrument in a single operation to save time and reduce the occurrence of infection without killing living tissue.

These and other objects are achieved in the present inventive method of use of a cordless medical laser by generating and focusing a single line wavelength laser light from a hand-held, self-contained, diode pumped, solid state laser instrument. Dental or surgical composites are cured by a focused, Q-switched, pulsed wavelength of laser light matching the optimum absorption wavelength of the composite material used. The focal point is moved through the composite from the deep layers to the surface to ensure complete curing. Sterilization is done by generating a UV wavelength from another laser chip in the same instrument in a divergent beam.

These and other objects and advantages of the present invention will become more apparent from the following drawing and the description of preferred embodiments.

DESCRIPTION OF PREFERRED EMBODIMENT

Figure 1:
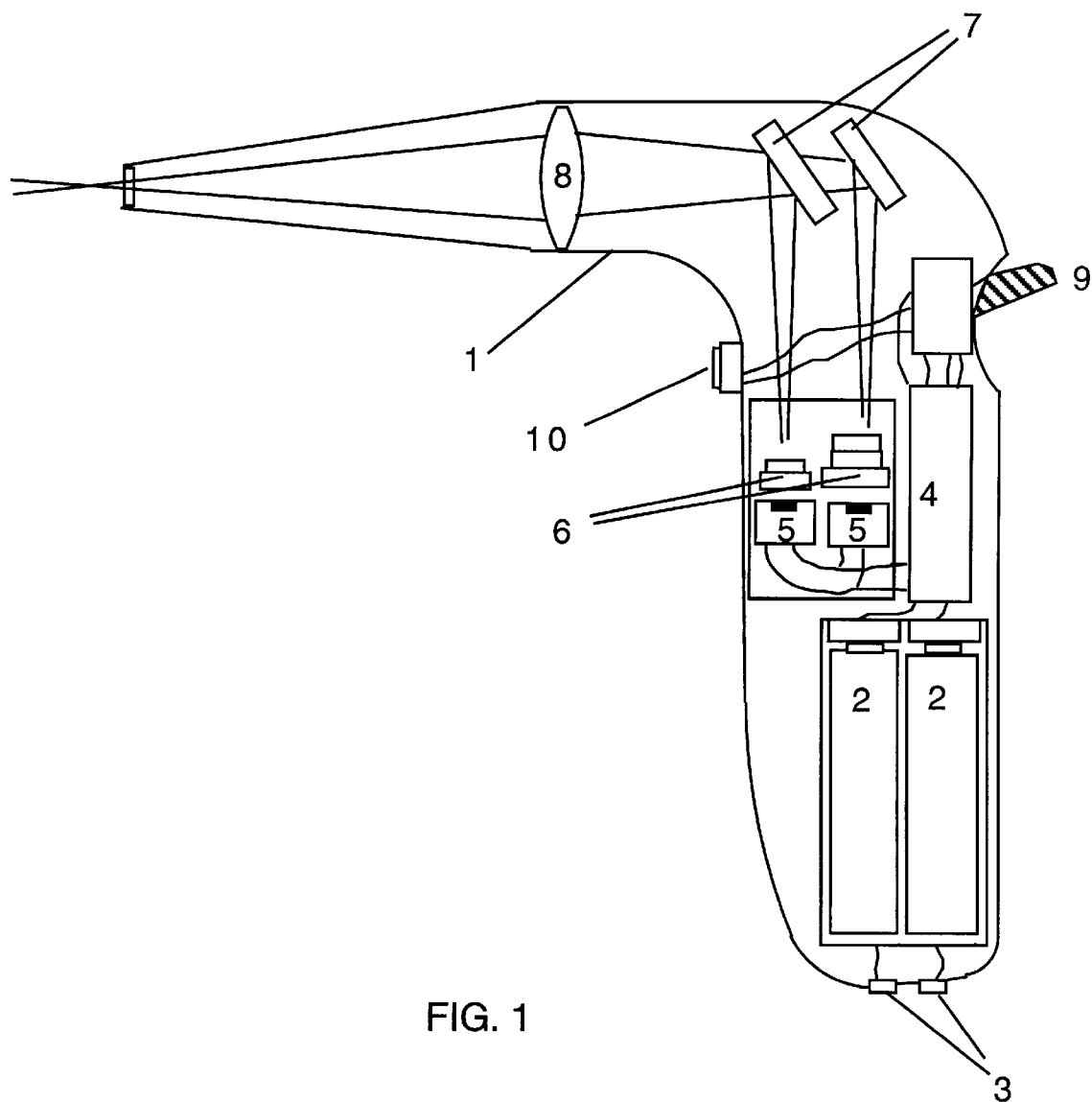
FIG. 1 is a longitudinal cross sectional view of the medical laser instrument used in the method of the present invention showing two different diode pumped solid state microchip lasers, one for curing composites and the other for sterilization of living biological tissue.

The present invention is a method for curing surgical and dental composites, and for sterilization of living biological tissue using a hand-held, cordless, portable, self-contained laser instrument such as the one shown in FIG. 1. First a living biological tissue site is exposed so that directed laser light can illuminate the site. A divergent beam of single band UV laser light is then generated by the solid state microchip 6, made of Nd:YVO$_4$, KTP, and LBO crystals, designated as Nd:YVO$_4$/KTP/LBO, being pumped by diode laser 5. In another example the UV microchip 6 is made of Nd:YAG/KNbO$_3$/BBO. The microchip 6 crystal laser materials may be optically contacted, bonded by thermal diffusion or bonded by optical epoxy. The solid state microchip 6 of the present invention is a solid state laser crystal material fabricated to have a volume of less than 1 cubic centimeter. A microchip 6 can consist of several such crystal materials all contained within the optical cavity. The output wavelength of the UV laser is at most 360 nm and, preferably selected in a range of 210 nm–360 nm and matched to the optimum differential absorption of the microbial cells to be killed and to the minimum absorption of healthy living tissue, so that the living tissue at the site of repair is not killed. The divergent beam of UV laser light is directed onto the living tissue site for a sufficient time to kill all microbial life forms which are contaminating the site. The beam is divergent so that it covers the site to be sterilized. Then, for the curing mode of operation, a sufficient quantity of a chosen photo-polymerizable medical composite material is placed at a site of repair and restoration. Then the instrument 1 is switched to the curing mode of operation by a switching means 9 just above the on/off switch 10. This activates pumping of at least a second chosen solid state laser microchip 6 to generate a selected wavelength of at most 480 nm. The wavelength is selected to be the maximum absorption wavelength of the material to be cured. The beam is focused through a lens 8 after being reflected from turning mirrors 7. The chosen microchip 6 in this example is one selected from the group consisting of Nd:YAG/KNbO$_3$ and Nd:YVO$_4$/KNbO$_3$. The focused beam is directed into the chosen composite light activated material for a sufficient time for curing to occur. The power consumption during laser operation is at most 10 watts, and the maximum laser output power is at least 20 m Watts. The output power is adjusted to the requirements of the targeted material by the diode laser driver electronics 4.

To enhance the completeness of curing, the focal point of the laser light is placed on the tissue/composite interface first, and then moved through the composite material to the surface, which is distal to the above interface. This eliminates air bubble entrapment and it enhances the bond between the composite material and the biological tissue to be repaired.

Since only one line of wavelength of laser light is generated by the microchip 6, no filters are needed and the power is used much more efficiently than in the prior art. So little power is required, that all of the components of the instrument 1 including the rechargeable batteries 2 with recharging electrodes 3, diode laser driver electronics 4, pumping diode lasers 5, microchips 6, mirrors 7, and lens 8 are housed in a unit hand-held, ergonomic, cordless, self-contained, portable, light-weight instrument housing, which has not been possible in the prior art. The microchips 6 are constructed out of any suitable lasing material not limited to solid state materials.

Q-switched, pulsed laser light is provided to further enhance efficiency and control of the curing process. A focused beam is superior to a collimated beam for curing due to the fact that light activation of deeper layers of photo-polymerizable medical composite material can be accomplished before the surface layer is cured.

The instrument 1 can be used only in the curing mode, and it can be used only in the sterilization mode. Alternatively, it is used first to sterilize a tissue site and then to cure a restorative surgical or dental light activated composite material. The switch 9 ensures that only one mode will be engaged at one time. This combined use saves a great deal of time in surgical and dental procedures while reducing the possibility of infection far below that in the prior art.

Accordingly, for all these reasons set forth, it is seen that the method of the present invention represents a great advancement in the art of composite curing and sterilization in surgery and dentistry, and has substantial commercial merit.

While there is shown and described herein certain specific process steps, structures, and methods, it will be manifest to those skilled in the art that modifications may be made without departing from the spirit and scope of the underlying inventive concept. The present invention shall not be limited to the particular process steps, structures, and methods herein described except by the scope of the appended claims.

What is claimed is:

1. A method of using a diode pumped solid state laser generation instrument for curing photo-polymerizable composite materials and for sterilization of living biological tissue useful in surgery, dentistry, and medicine comprising the steps of:

exposing a biological tissue site to be sterilized sufficiently so that a directed laser light can illuminate said site;

generating a divergent beam of a UV wavelength laser light of a single selected wavelength within a hand-held, self-contained, diode pumped solid state laser generation instrument by pumping a first chosen solid state laser microchip with a diode laser and by passing said laser light generated from said microchip through a lens;

directing said divergent beam onto a biological living tissue site to be sterilized for a sufficient time to kill micro-biological life forms contaminating said site, the wavelength of said light emitted from said first chosen microchip being at most 360 nm and selected to be the maximum absorption wavelength of the contaminating life forms;

placing a quantity of a chosen photo-polymerizable medical composite material at a site of repair, said quantity being sufficient to effect repair;

switching said instrument to a curing mode of operation by a switching means to activate pumping of at least a second chosen solid state laser microchip within said instrument;

generating and focusing a single band blue wavelength laser light beam of a selected wavelength in said instrument and passing said light beam through a focusing lens, said selected wavelength generated by said second chosen microchip being at most 480 nm;

directing the focused single band wavelength laser light from said instrument into said material for a sufficient time to effect curing of said material, said wavelength being selected to be the maximum absorption wavelength of said chosen composite material.

2. The method according to claim 1 wherein the step of directing said laser light into said material is done by first placing the focal point of said focused laser light at a biological tissue interface with said material and then by moving said focal point from said interface in a direction toward the surface of said material distal to said interface and by ending at said surface distal to said interface, such that said material is cured at said interface initially and at said surface lastly.

3. The method according to claim 1 wherein the said instrument comprises a pumping diode laser housed together with said first and said second chosen microchips and with a rechargeable diode laser power supply.

4. The method according to claim 3 wherein said laser light is Q-switched, pulsed laser light, the maximum power of said laser light is adjusted to the requirements of the targeted substance.

* * * * *